United States Patent
Veverka et al.

(10) Patent No.: US 7,714,133 B2
(45) Date of Patent: May 11, 2010

(54) METHOD FOR MANUFACTURING CRYSTALLINE FORM I OF CLOPIDOGREL HYDROGEN SULPHATE

(75) Inventors: Miroslav Veverka, Bratislava (SK); Stefan Vodny, Bratislava (SK); Eva Veverkova, Bratislava (SK); Josef Hajicek, Prague (CZ); Hana Stepankova, Cesky Brod (CZ)

(73) Assignee: Zentiva, k.s., Prague (CZ)

( * ) Notice: Subject to any disclaimer, the term of this patent is extended or adjusted under 35 U.S.C. 154(b) by 889 days.

(21) Appl. No.: 10/525,341

(22) PCT Filed: Aug. 26, 2003

(86) PCT No.: PCT/CZ03/00049

§ 371 (c)(1),
(2), (4) Date: Jul. 6, 2005

(87) PCT Pub. No.: WO2004/020443

PCT Pub. Date: Mar. 11, 2004

(65) Prior Publication Data

US 2006/0041136 A1 Feb. 23, 2006

(30) Foreign Application Priority Data

Aug. 27, 2002 (CS) .................. 2002-2906

(51) Int. Cl.
*C07D 495/04* (2006.01)
(52) U.S. Cl. ..................... 546/114; 514/301
(58) Field of Classification Search ............. 546/114; 514/301
See application file for complete search history.

(56) References Cited

U.S. PATENT DOCUMENTS

| 4,847,265 A | 7/1989 | Badorc et al. | 546/114 |
| 6,429,210 B1 | 8/2002 | Castro et al. | 546/114 |
| 6,767,913 B2 * | 7/2004 | Lifshitz et al. | 514/301 |
| 7,074,928 B2 * | 7/2006 | Lifshitz-Liron et al. | 546/119 |
| 7,291,735 B2 * | 11/2007 | Mukarram et al. | 546/114 |
| 2008/0051581 A1 * | 2/2008 | Mukarram et al. | 546/114 |

FOREIGN PATENT DOCUMENTS

WO WO2005/012300 * 2/2005

OTHER PUBLICATIONS

Kirk-Othmer "Crystallization . . ." Kirk-Othmer encyclopedia of Chemical Technology. vo. 8, p. 95-147 (2002).*

* cited by examiner

*Primary Examiner*—Celia Chang
(74) *Attorney, Agent, or Firm*—Oblon, Spivak, McClelland, Maier & Neustadt, L.L.P.

(57) ABSTRACT

A method for manufacturing hydrogen sulphate (alpha S) of the alpha-(2-chlorophenyl)-6,7dihydrothieno[3,2-c]pyridine-5(4H)-acetic acid methyl ester (clopidogrel hydrogen sulphate) of formula I, in crystalline Form I, wherein the compound of formula is separated out of a solution of clopidogrel in the form of the free base or salt in a solvent selected from the series of primary, secondary or tertiary C1-C5 alcohols, their esters with C1-C4 carboxylic acids, or optionally of mixtures thereof.

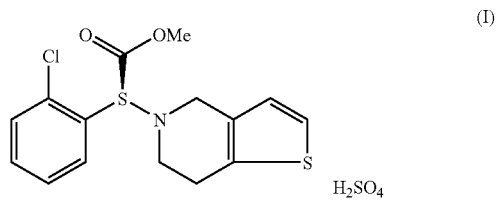

(I)

7 Claims, 5 Drawing Sheets

METHOD FOR MANUFACTURING CRYSTALLINE FORM I OF CLOPIDOGREL HYDROGEN SULPHATE

TECHNICAL FIELD

The invention relates to a new method for manufacturing hydrogen sulphate (alpha S) of the alpha-(2-chlorophenyl)-6,7-dihydro-thieno[3,2-c]pyridine-5(4H)-acetic acid methyl ester (clopidogrel hydrogen sulphate) in its crystalline Form I.

BACKGROUND ART

Hydrogen sulphate (alpha S) of the alpha-(2-chlorophenyl)-6,7-dihydro-thieno[3,2-c]pyridine-5(4H)-acetic acid methyl ester (clopidogrel hydrogen sulphate) of formula I

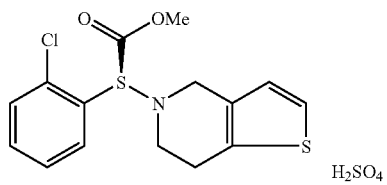

is an anti-thrombotic agent that has been described in patent CZ 274 420 (EP 281 459), dealing with the technology for manufacturing dextrorotatory S enantiomer. The manufacturing method disclosed in the cited patent dwells in reacting the racemic mixture with optically active camphor sulphonic acid and subsequent separating the diastereoisomer.

The respective salt of clopidogrel with camphor sulphonic acid is transformed with sodium hydrogen carbonate solution in methylene chloride environment into the optically active base, which is obtained by evaporation of the solvent.

The evaporation residue—the optically active base of clopidogrel—is dissolved in acetone, where it is transformed into hydrogen sulphate by adding drops of an equivalent amount of sulphuric acid, under cooling with crushed ice. The melting temperature of the resulting precipitate is stated as 184° C.

The specification of CZ 274 420 (EP 281 459) does not deal with the crystalline form of clopidogrel hydrogen sulphate prepared in this way. A newer patent application, CZ 2000-4637 (WO 99/65915) gives a description of crystalline Forms I and II of clopidogrel hydrogen sulphate. According to this more recent patent application, the precipitation method described in CZ 274 420 (EP 281 459) had led to crystalline Form I. The above application defines an allegedly new crystalline form, Form II. The process for obtaining Form II according to example 1A of this application dwells in introduction of the salt of clopidogrel with camphor sulphonic acid into methylene chloride and its transformation into the base with a solution of potassium carbonate. Methylene chloride is evaporated and the evaporation residue is dissolved in acetone. By adding sulphuric acid, the hydrogen sulphate precipitates out of acetone.

The methods leading—according to the application CZ 2000-4637 (WO 99/65915)—to Form II, are thus very similar to those leading to Form I according to the same application. Since, moreover, the application defines Form II as thermodynamically more stable, it is obvious that the known methods allegedly resulting in Form I will be poorly reproducible.

It can be assumed that even a small change in conditions will result in Form II instead of expected Form I. The Form I under generation can, under these circumstances, transform spontaneously into Form II and it can be expected that it will be at least contaminated with Form II.

The above stated expectations have been proven experimentally.

The present invention provides a reliable method for obtaining Form I of clopidogrel hydrogen sulphate without detectable impurity of Form II.

DISCLOSURE OF THE INVENTION

This invention relates to a method for manufacturing crystalline Form I of clopidogrel hydrogen sulphate, consisting in crystallisation or precipitation of this Form from a solvent selected from the series of C1-C5 alcohols or their esters with C1-C4 acids, optionally of mixtures of alcohols and esters.

The manufacturing method described in the prior art thus allows a non-specific preparation of Form I. It has now been found out that if clopidogrel hydrogen sulphate is allowed to crystallise by the procedure according to this invention, Form I having a high and defined content can be obtained in a reproducible way. The substance of this invention is a process for manufacturing crystalline Form I of clopidogrel hydrogen sulphate, which method resides in:

1. transforming the salt of clopidogrel with camphor sulphonic acid, in an organic solvent medium, using a solution of a weak inorganic base, into an optically active base;
2. isolating, from the organic phase, the corresponding clopidogrel base by evaporating the solvent, and subsequent dissolving said base in a solvent selected from the series of C1-C5 alcohols or their esters with C1-C4 acids, optionally of mixtures of alcohols and esters, and cooling the mixture;
3. adding sulphuric acid and inoculating the mixture with Form I of clopidogrel hydrogen sulphate;
4. stirring the crystallised mixture at a temperature between −5 and 15° C., filtering and drying the crystals, thus obtaining Form I of clopidogrel hydrogen sulphate.

According to another characteristic, crystalline Form I of clopidogrel hydrogen sulphate can be produced in an alternative procedure, residing in:

1. dissolving clopidogrel hydrogen sulphate in a solvent selected from the series of C1-C5 alcohols or their esters with C1-C4 acids, optionally of mixtures of alcohols and esters, at the boiling temperature of the respective solvents;
2. filtering the mixture through a filter with an opening size of 0.1 to 1 μm;
3. cooling the solution down, filtering and drying under reduced pressure, thus obtaining Form I of clopidogrel hydrogen sulphate.

The quality of clopidogrel hydrogen sulphate of Form I without detectable contamination by Form II, obtained in accordance with this invention, is documented by the following measurements by means of common technologies.

A characteristic powder diffractogram of the powder of thus obtained Form I of clopidogrel hydrogen sulphate is shown in FIG. 1; the table gives the inter-grid distances and relative intensities (the percentages of the most intensive line). The X-ray diffraction profile of the powder was assessed in the apparatus PHILIPS PW1730/PW1050, Cu radiation (K alpha) Ni filter, with automated data collection, voltage: 40 kV, current: 25 mA, with the advance rate of the goniometer of ½° per minute and the time constant of 1.

The quality of thus manufactured Form I of clopidogrel hydrogen sulphate has been confirmed by Fourier Transform infrared spectroscopy (FTIR), shown in FIG. 2. The spectra were taken in the spectrometer Nicolet USA, type: Impact 410. Conditions of measurement: KBr tablet technology, 16 scan, resolution: 4/cm (reciprocal cm), background KBr tablet.

An analysis of differential enthalpy (DSC) has been performed in the apparatus Perkin Elmer DSC 7, calibrated to In. For calorimetric assessment, 1.725 mg were used, in an Al cup, with the temperature ranging from 40 to 200° C., the speed of heating: 10° C./min. The melting point and a characteristic DSC curve is shown in FIG. 3.

Using combination of the above methods, the detection limit of the alternative crystalline form remains reliably under 2%. This method thus ensures that the content of the polymorph is 98% at minimum.

EXAMPLES

Example 1

Figure 1:
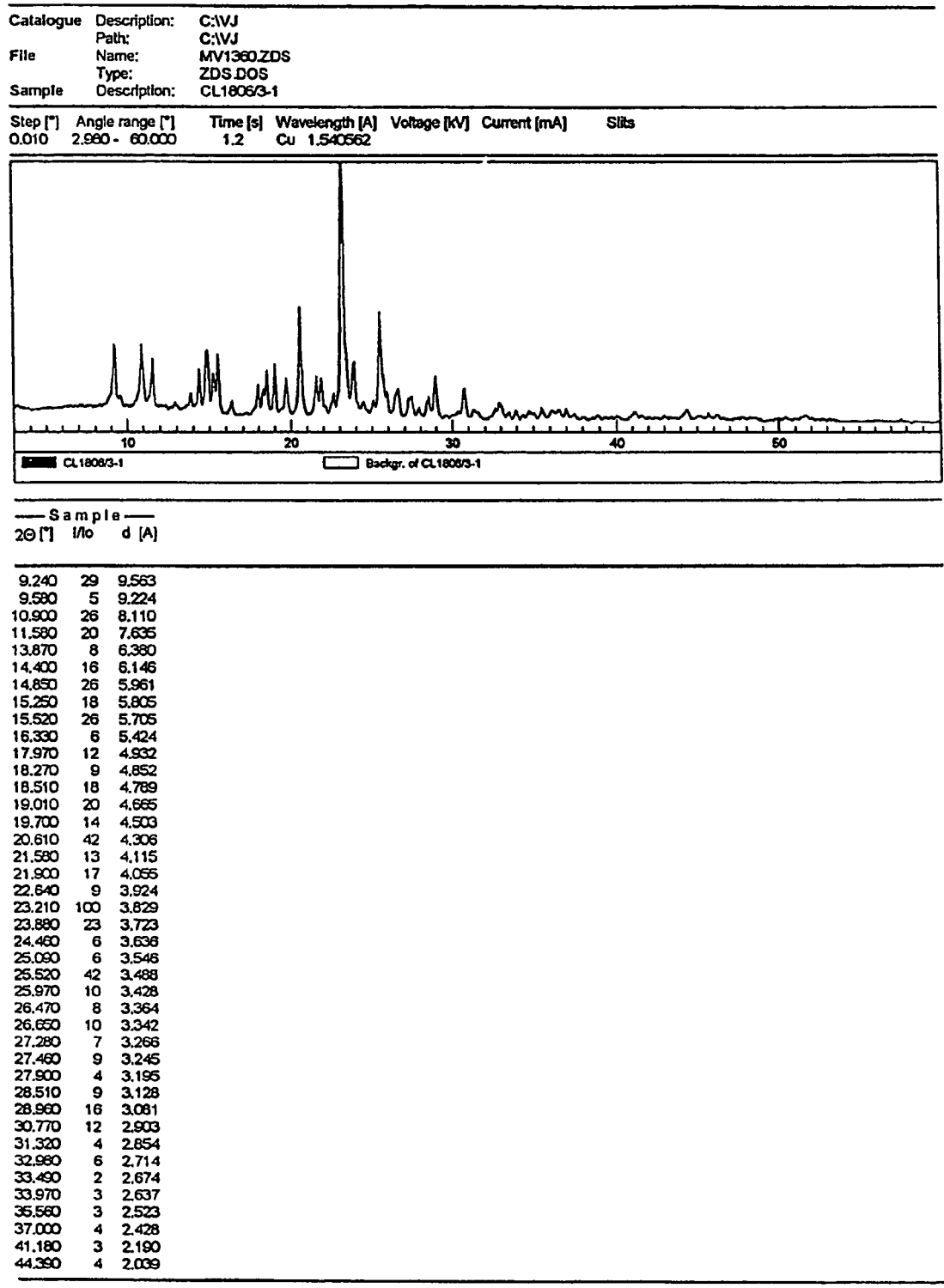
FIG. 1 represents an X-ray diffractogram of Form I of clopidogrel hydrogen sulphate according to Example 4.
Figure 2:
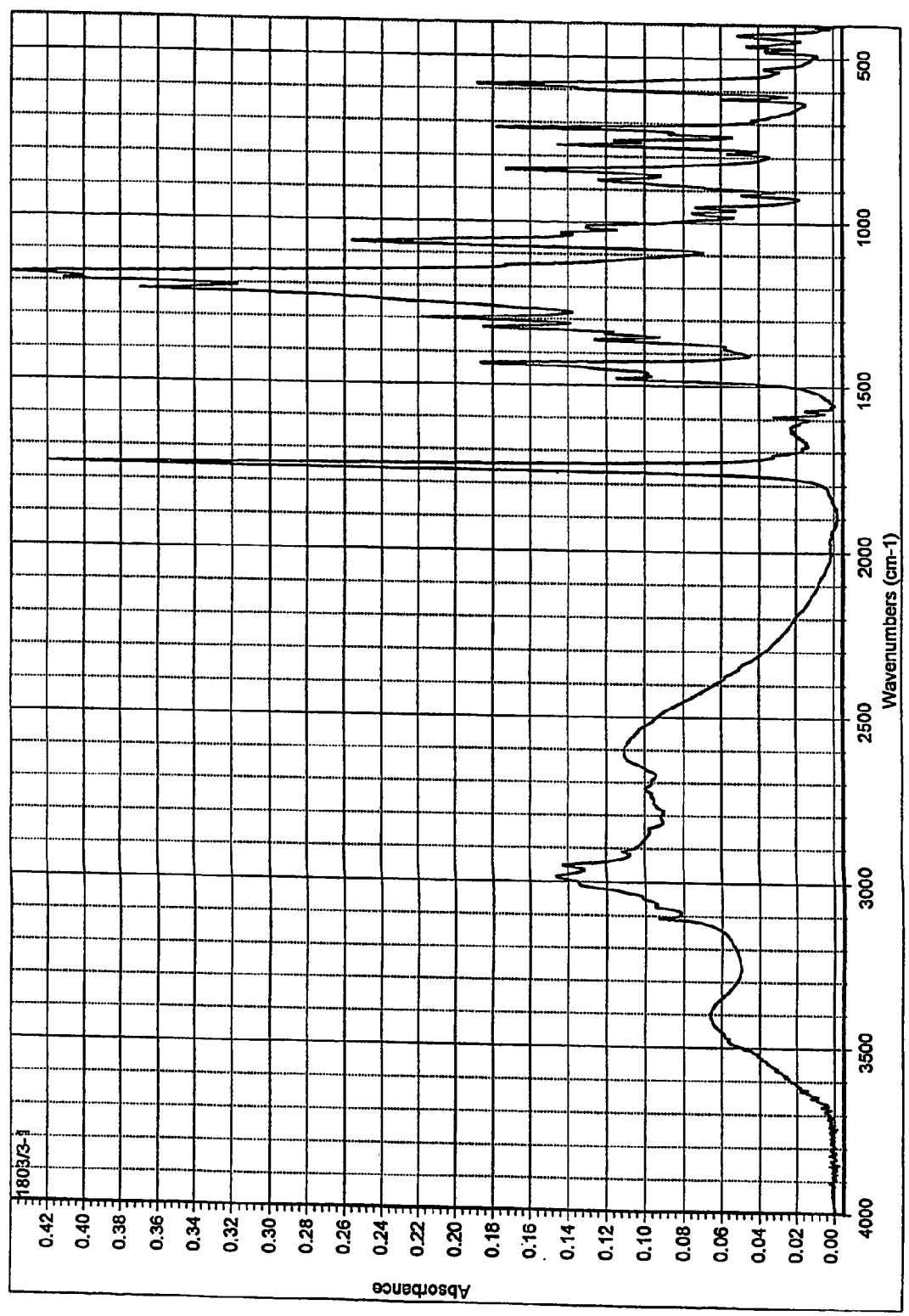
FIG. 2 shows its spectrogram obtained by Fourier Transform IR spectrometry (FTIR) and, FIG. 3 is a record of differential calorimetry.
Figure 3:
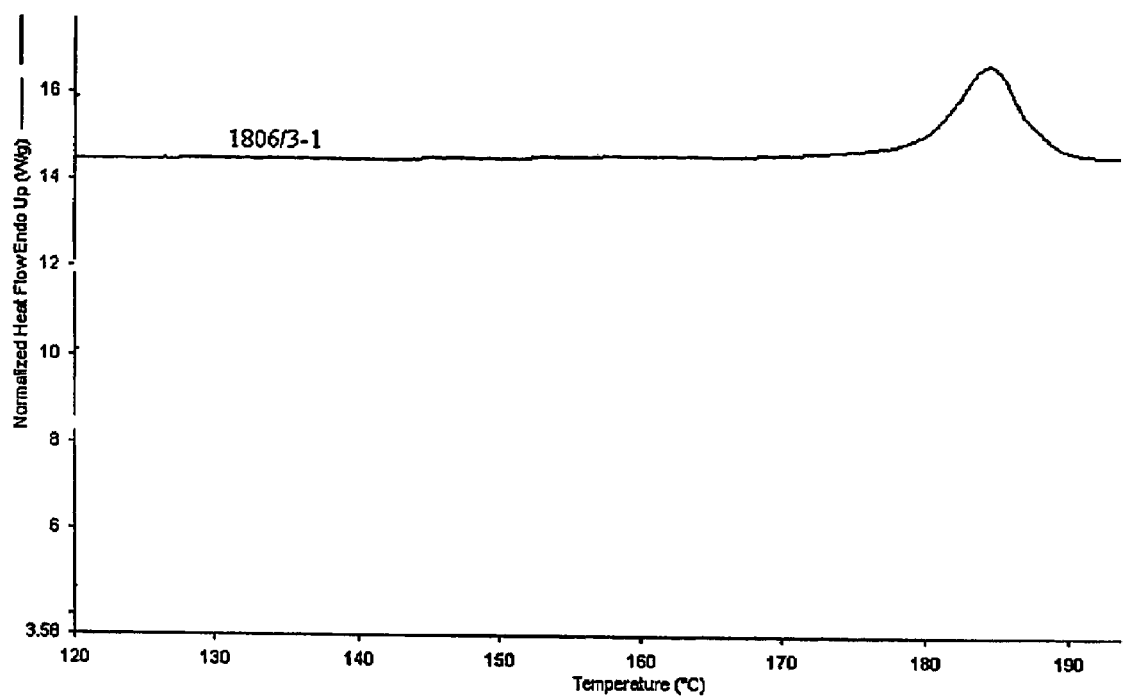

2.26 gram of clopidogrel base are placed into a flat-bottom flask, equipped with a thermometer and a magnetic stirrer, and dissolved in 32 ml of dried i-propanol. Under stirring, the solution is cooled down to 0 to −5° C. Then, 0.33 ml of 98% sulphuric acid are added ($\rho$-1.8361 g.cm$^{-3}$) and inoculated with crystals of Form I. The mixture is stirred at the above stated temperature for 2.5 hours, whereby in about 1 hour the look of the separated crystalline phase changes as it gradually passes into the solution. The temperature of the mixture is increased to 10° C. and it is inoculated with Form I crystals again after about 0.5 hour. The mixture is stirred until the crystalline phase separates at a temperature between 10 and 15° C. for 1.5 to 2 hours, and then at −5° C. for 8 hours. The product is filtered off on fritted glass S-2 and dried with a stream of air. 1.7 g of clopidogrel hydrogen sulphate Form I with minimal polymorph purity of 98% and having the melting point of 185 to 187° C. are obtained.

0.5 g of clopidogrel hydrogen sulphate Form II, having the melting point of 177 to 179° C., are separated out of the mother liquors upon standing at 25° C.

Example 2

25 grams of clopidogrel hydrogen sulphate are placed into a flask, equipped with a magnetic stirrer and a reflux condenser, and dissolved in 1150 ml butyl acetate under reflux in an inert gas atmosphere. The slightly turbid solution is filtered and cooled down to 0 to −2° C. under stirring. It is put aside into a refrigerator and, after 6 hours, the precipitated product is immediately sucked off on a frit S-2. After drying under reduced pressure, Form I of clopidogrel hydrogen sulphate having the melting point of 184 to 186° C. is obtained.

Example 3

20 grams of clopidogrel base are placed into a flat-bottom flask, equipped with a thermometer and a magnetic stirrer, and dissolved in 140 ml dried i-propanol and 140 ml butyl acetate. Under stirring, the solution is cooled down to 0 to −2° C. Subsequently, 2.9 ml of 98% sulphuric acid are added ($\rho$-1.8361 g.cm$^{-3}$). The mixture is stirred at the above stated temperature for 1 hour, at 5° C. for 2 hours and at −5° C. for 8 hours. The product is filtered off on fritted glass S-2 and dried at a reduced pressure. 14.5 g of clopidogrel hydrogen sulphate Form I, showing the melting point of 184 to 186° C., are obtained.

From the mother liquors, clopidogrel hydrogen sulphate Form II, having the melting point of 177 to 179° C., is separated upon standing at 25° C.

Example 4

1.84 gram of clopidogrel base are placed into a flat-bottom flask, equipped with a thermometer and a magnetic stirrer and dissolved in 26 ml dried i-propanol under boiling. Under stirring, the solution is cooled down to 0° C. Then, 0.33 ml of 98% sulphuric acid are added ($\rho$-1.8361 g.cm$^{-3}$) and inoculated with crystals of Form I. The mixture is stirred at the above stated temperature for 2.5 hours, whereby in about 1 hour the look of the separated crystalline phase changes as it gradually passes into the solution. The temperature of the mixture is increased to 10° C. and it is inoculated with Form I crystals again after about 0.5 hour. The mixture is stirred until the crystalline phase separates at the temperature of 10° C. for 1.5 to 2 hours, and then at −1° C. for 8 hours. The product is filtered off on fritted glass S-2 and dried with a stream of air. 1.8 g of clopidogrel hydrogen sulphate Form I having the melting point of 184 to 186° C. are obtained.

Example 5

56.9 g clopidogrel base are dissolved in 570 ml of n-butyl acetate and placed in a three-neck round flask, equipped with a thermometer, a KPG stirrer and a dropping funnel. Under mixing, the butyl acetate solution is cooled down to 0 to +5° C. in a water-and-ice bath. The solution is inoculated with crystals of clopidogrel Form I. Under intensive stirring, 9.71 ml of concentrated sulphuric acid (97%) (1.5 equiv.) are added dropwise into the cooled-down solution such that the temperature of the reaction mixture does not exceed +5° C. After acidifying, the reaction mixture is heated to +10° C. and stirred at this temperature for 3 hours, after which period the temperature of crystallisation is increased to +20 to +24° C., at which temperature stirring is continued for another 18 hours.

After said period the obtained crystalline fraction is filtered through fritted glass (S2) and dried at a temperature up to 25° C.

Figure 4:
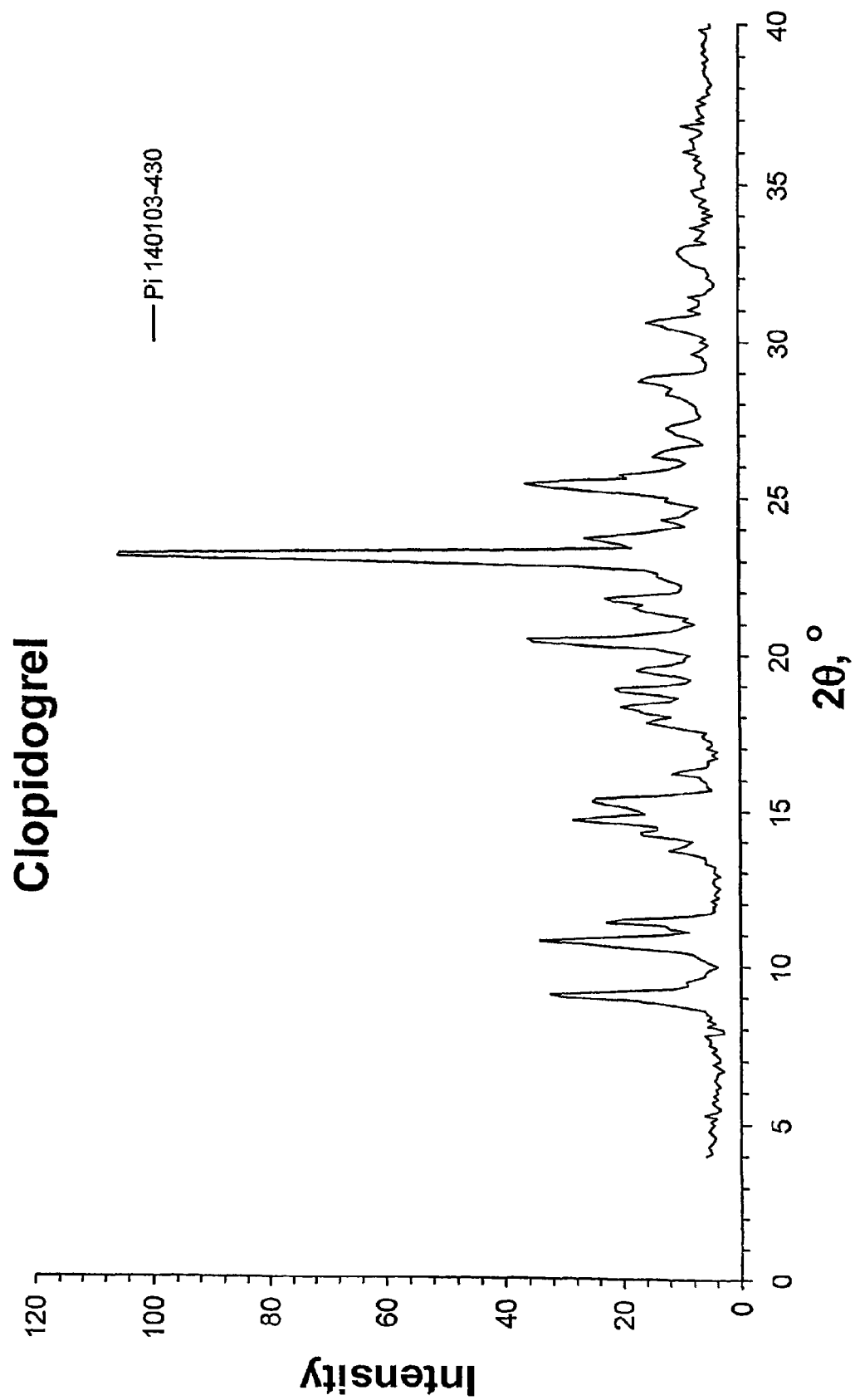
FIG. 4 represents an X-ray diffractogram of the product according to Example 5, and FIG. 5 relates to the product of Example 6.

In this way, 63.0 g (84.8% of theory) of clopidogrel hydrogen sulphate Form I are obtained. The X-ray diffractogram corresponds to Form I (FIG. 4).

Example 6

12.63 g clopidogrel base are dissolved in 126 ml of n-butyl acetate and placed in a three-neck round flask, equipped with a thermometer, a KPG stirrer and a dropping funnel. Under stirring, the butyl acetate solution is cooled down to 0 to +5° C. in a water-and-ice bath. The solution is inoculated with crystals of clopidogrel Form I. Under intensive stirring, 2.4 ml of concentrated sulphuric acid (98%) (1.1 equiv.) are added dropwise into the cooled-down solution such that the temperature of the reaction mixture does not exceed +5° C. After acidifying, the reaction mixture is heated to +10° C. and stirred at this temperature for 3 hours, after which period the temperature of crystallisation is increased to +20 to +23° C., at which temperature stirring is continued for another 19 hours.

After said period the obtained crystalline fraction is filtered through fritted glass (S2) and dried at a temperature up to 25° C.

Figure 5:
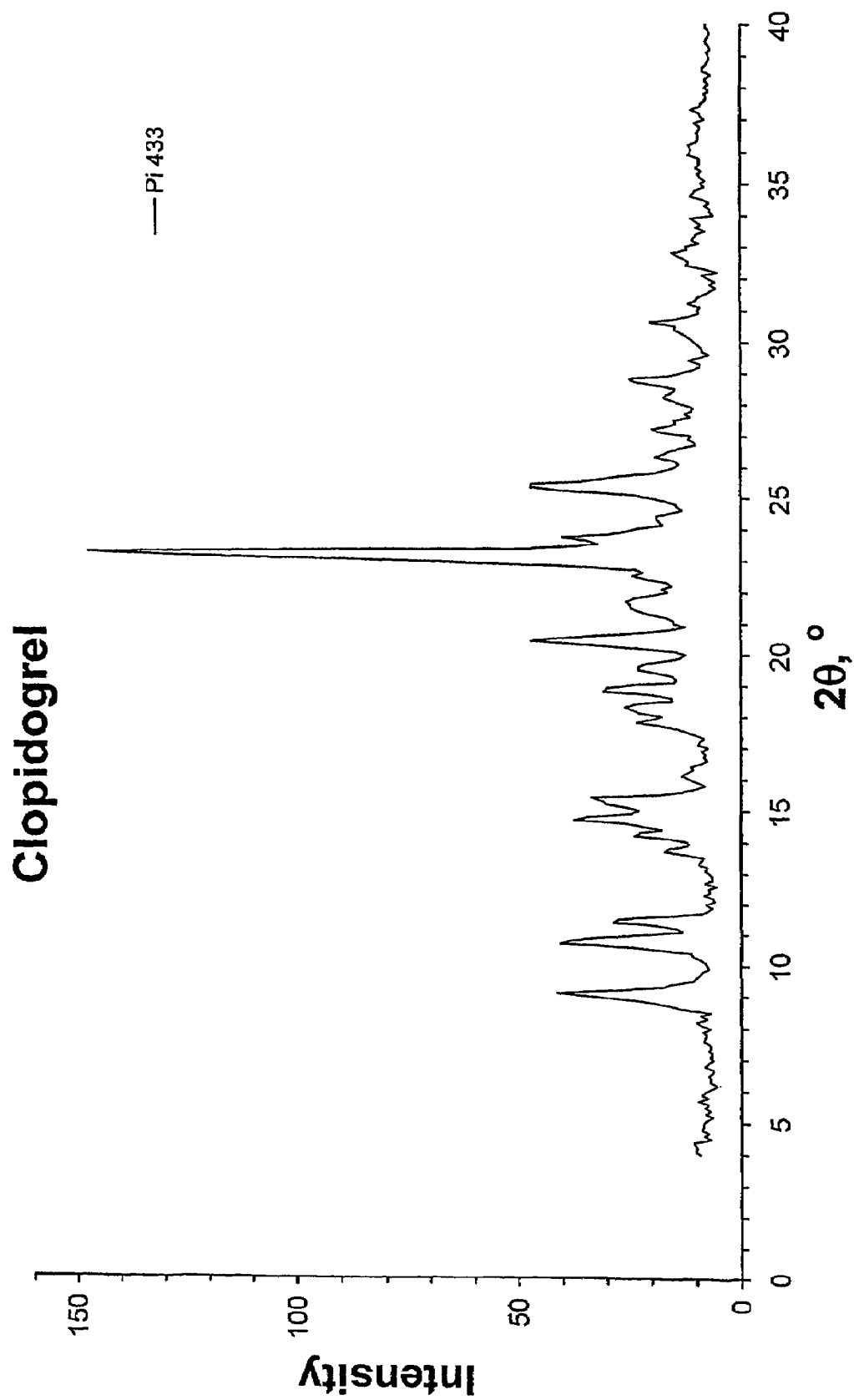

In this way, 15.16 g (78.0% of theory) of clopidogrel hydrogen sulphate Form I are obtained. The X-ray diffractogram corresponds to Form I (FIG. 5).

The invention claimed is:

1. A method for manufacturing hydrogen sulphate (alpha S) of the alpha-(2-chlorophenyl)-6,7-dihydro-thieno[3,2-c]pyridine-5(4H)-acetic acid methyl ester (clopidogrel hydrogen sulphate) of formula I

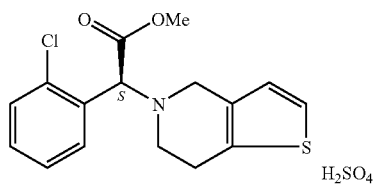

(I)

in crystalline Form I, said method comprising separating crystalline Form I of the compound of formula I out of a solution of clopidogrel in the form of the free base in a solvent selected from the group consisting of 2-propanol and n-butyl acetate by adding 0.6 to 1.1 equivalent of sulphuric acid at 0 to −5° C. when 2-propanol is the solvent or at 0 to +5° C. when n-butylacetate is the solvent, and then stirring the mixture at a temperature between −5 and 15° C.

2. The method according to claim 1, wherein the crystalline Form I of the compound of formula I is precipitated out of a solution of clopidogrel in the form of the free base in 2-propanol.

3. The method according to claim 2, wherein the crystalline Form I is precipitated out of a solution of clopidogrel in the form of the free base in 2-propanol at a temperature between −5 and 15° C. after the solution is inoculated with crystals of Form I.

4. The method according to claim 1, wherein crystalline Form I of the compound of formula I is precipitated out of a solution of clopidogrel base in n-butylacetate.

5. The method according to claim 4, wherein crystalline Form I of the compound of formula I is precipitated out of a solution of clopidogrel in the form of the free base in n-butyl acetate at a temperature between −5 and 15° C. after the solution is inoculated with crystals of Form I.

6. A method for manufacturing hydrogen sulphate (alpha S) of the alpha-(2-chlorophenyl)-6,7-dihydro-thieno[3,2-c]pyridine-5(4H)-acetic acid methyl ester (clopidogrel hydrogen sulphate) of formula I

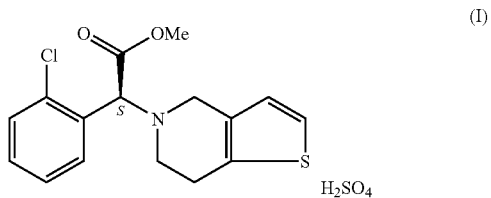

(I)

in crystalline Form I, said method comprising separating crystalline Form I of the compound of formula I out of a solution of clopidogrel in the form of the free base in n-butyl acetate by adding 1.1 to 1.5 equivalent of concentrated sulphuric acid at 0 to +5° C., and then stirring the mixture at a temperature of 10 to 24° C.

7. A method for manufacturing hydrogen sulphate (alpha S) of the alpha-(2-chlorophenyl)-6,7-dihydro-thieno[3,2-c]pyridine-5(4H)-acetic acid methyl ester (clopidogrel hydrogen sulphate) of formula I

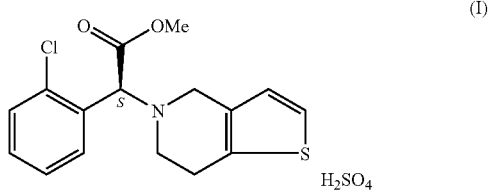

(I)

in crystalline Form I, said method comprising separating crystalline Form I of the compound of formula I out of a solution of clopidogrel in the form of the free base in 2-propanol by adding 0.6 to 1.1 equivalent of concentrated sulphuric acid at 0 to −5° C., and then stirring the mixture at a temperature between −5 and 15° C.

\* \* \* \* \*